United States Patent [19]

Pohndorf

[11] Patent Number: 4,672,979
[45] Date of Patent: Jun. 16, 1987

[54] SUTURE SLEEVE ASSEMBLY

[75] Inventor: Peter J. Pohndorf, Miami Shores, Fla.

[73] Assignee: Cordis Corporation, Miami, Fla.

[21] Appl. No.: 824,233

[22] Filed: Jan. 30, 1986

[51] Int. Cl.⁴ .............................................. A61N 1/05
[52] U.S. Cl. ................................ 128/784; 128/419 P; 604/175
[58] Field of Search .............................. 128/784–786, 128/419 P, DIG. 26, 334 C; 604/174, 175, 178, 179, 905

[56] References Cited

U.S. PATENT DOCUMENTS

| | | | |
|---|---|---|---|
| 3,241,554 | 3/1966 | Coanda | 128/DIG. 26 |
| 4,114,626 | 9/1978 | Beran | 128/DIG. 26 |
| 4,287,891 | 9/1981 | Peters | 604/174 |
| 4,553,961 | 11/1985 | Pohndorf et al. | 604/175 |

FOREIGN PATENT DOCUMENTS 459238  4/1975  U.S.S.R. ............................ 604/178

Primary Examiner—Lee S. Cohen
Attorney, Agent, or Firm—George H. Gerstman

[57] ABSTRACT

A suture sleeve assembly is provided for placement around an elongated lead body, for example a cardiac pacing lead. The assembly anchors the lead body in position relative to the adjacent tissue, and comprises a tubular sleeve and a collet member. The collet member defines a plurality of axially extending legs residing in the bore of the tubular sleeve. The inner surfaces of the legs define frictional gripping members to engage a lead body positioned within the sleeve assembly. Structure is also provided for retaining the collet member in a position with the legs occupying the bore of the tubular sleeve.

6 Claims, 4 Drawing Figures

SUTURE SLEEVE ASSEMBLY

BACKGROUND OF THE INVENTION

In the implantation of a pacing lead into the atrium or ventricle of the heart, the physician makes an incision in the wall of the vein of choice. The pacing lead, with an elastomeric sleeve thereon, is inserted into a vein such as the cephalic or external jugular vein. The tip electrode of the lead is positioned into the atrium or ventricle by advancing the pacing lead through the vein into the desired heart chamber.

Following this, the end of the pacing lead opposite the tip electrode is tunneled to the prepared pacer pocket which the surgeon has made between the muscle and the overlying skin. After determining that the electrode position is satisfactory, the lead is connected to a pacer unit, which is then implanted in the pocket.

At the site of exit of the pacing lead from the vein through which it passes, the pacing lead body is typically anchored to underlying muscle, to prevent slippage of the pacing lead and its tip electrode from the desired position in the atrium or ventricle. However, the placement of sutures around the pacing lead body has been found to sometimes cause damage to the lead body insulating material. To avoid this, a suture sleeve may be provided which fits tightly around the lead body at the point where the sutures are applied, to retain the lead in the desired position without damaging its insulation. Such suture sleeves of the prior art may be provided with a pair of spaced, circumferential grooves for receiving the sutures, which are passed through adjacent tissue and tied within one of the grooves, securing the suture sleeve to the sutures, and securing it as well to the underlying tissue.

However, it has been found that the lead can slip axially through the suture sleeve on occasion. The result of this is that the tip electrode of the pacing lead can be moved away from the site of stimulation which, of course, can result in a failure of the entire system.

In accordance with this invention a suture sleeve is provided to protect a lead body, which may be an insulated electric lead, a fragile catheter, or the like from damage which may result upon the direct application of sutures to the lead body. The suture sleeve of this invention provides greatly improved frictional retention of the lead body, significantly eliminating the chance of axial sliding of the lead body through the suture sleeve.

DESCRIPTION OF THE INVENTION

In this invention, a suture sleeve assembly is provided for placement around and protection of an elongated lead body, to anchor the lead body in position relative to the adjacent tissue in which it is implanted. Examples of lead bodies which may be used with the suture sleeve assembly of this invention include cardiac pacing leads or fragile catheters as described above, a spinal lead for communicating with the epidural space of the spinal cord, or any other elongated, implantable structure which needs the protective and positioning function of the suture sleeve of this invention.

The suture sleeve comprises a tubular sleeve which is preferably resilient or elastomeric, and a collet member. The collet member may define a plurality of axially extending legs residing in the bore of the tubular sleeve. The inner surface of the legs, in turn, define frictional gripping member to engage a lead body positioned within the sleeve assembly. Means are provided for retaining the collet member in a position with the legs occupying the bore of the tubular sleeve.

For use, a lead body is threaded through the collet member. The legs of the collet member are then inserted into the tubular sleeve, with the inner diameter of the tubular sleeve being so proportioned that the collet member legs are flexed inwardly into frictional gripping relation with the lead body. Thus, the increased frictional retention of the suture sleeve assembly of this invention greatly reduces the possibility that the lead body can move axially through the suture sleeve.

The tubular sleeve may define suture-receiving channel means on its outer surface to facilitate its retention in position by sutures, which bind it to the adjacent tissue. Also, the collet member preferably defines outwardly extending hook members positioned adjacent the free ends of the legs. A retention flange is positioned on the end of the collet member opposed to the free ends. Thus, the tubular sleeve may be proportioned whereby the legs pass through the sleeve to permit the hook members to engage one end thereof, while the retention flange engages the other end of the sleeve. Thus the collet member may be firmly retained in a fixed position relative to the tubular sleeve.

DESCRIPTION OF SPECIFIC EMBODIMENT

Figure 1:
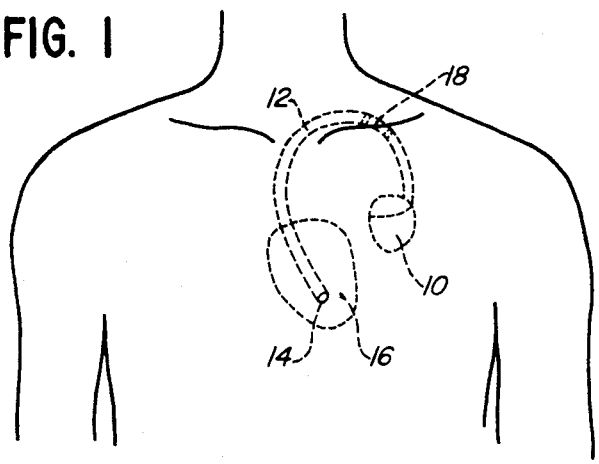
FIG. 1 is an elevational view of an upper torso of a patient showing a pacing lead exending between a pacer and the heart, with the lead being retained in position by an implanted suture sleeve of this invention.

Referring to the drawings, FIG. 1 shows a pacer system including a pacer 10, and a pacer lead 12 extending therefrom and terminating in an electrode 14 positioned within the heart 16 of the patient. Lead 12 passes through suture sleeve 18 of this invention which, in turn is sutured into the surrounding tissue to help position and stabilize the location of lead 12 and electrode 14.

Figure 4:
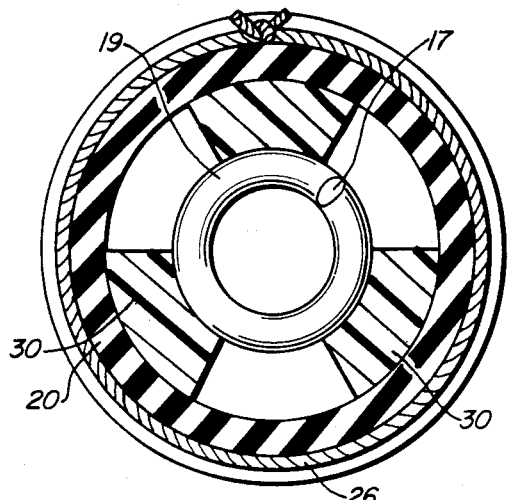
FIG. 4 is a transverse sectional view taken along line 4—4 of FIG. 2.
Figure 2:
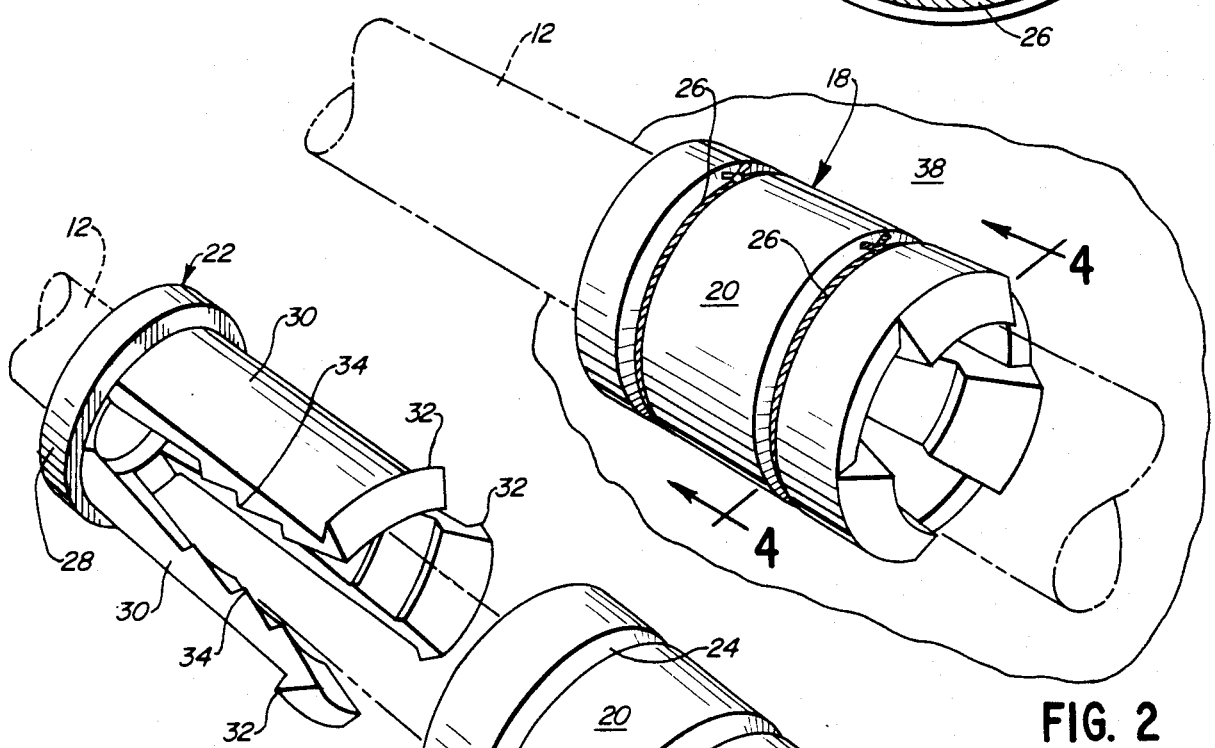
FIG. 2 is an enlarged, perspective view of the suture sleeve of this invention.
Figure 3:
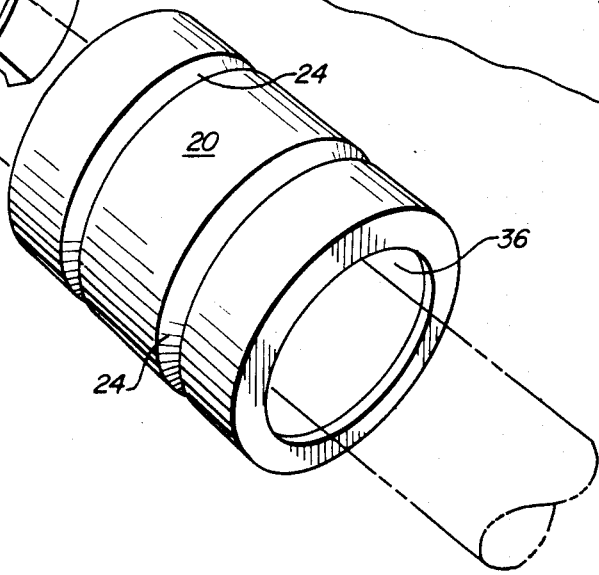
FIG. 3 is a perspective view of the disassembled suture sleeve assembly of FIG. 2.

FIGS. 2 through 4 show details of the pacer lead and suture sleeve assembly of this invention. Lead 12 comprises a typically coiled conductor wire 17, covered by insulating coating 19 of silicone rubber or the like. As shown, suture sleeve assembly 18 comprisese a tubular sleeve 20 which is preferably elastomeric, being made of silicone rubber or other resilient material, and collet member 22, which fits inside of sleeve 20.

Sleeve 20 defines a pair of circumferential suture-receiving channels 24 with the sutures 26 being shown in FIG. 2 to occupy channels 24 for retention of sleeve assembly 18 in desired position against tissue 38, typically near the point where lead 12 passes through the blood vessel wall. Lead body 12 is shown to extend through suture sleeve assembly 18, and to be retained in position thereby.

Collet member 22 may be relatively stiff, being made of appropriate plastic or metal, defining annular retention flange 28 through which lead body 12 passes. A portion of lead body 12 is broken away at its point of passage through annular flange 28.

Annular flange 28 carries three (or any desired number) axially extending legs 30 which are connected to flange 28 at one end and are shown to carry outwardly extending hook members 32 at their other ends. At least one of legs 30 and preferably all carry on their inner surfaces frictional gripping members 34, which may be simple serrations or the like, to press against the outer surface of lead body 12 to increase the frictional retention thereof within the suture sleeve assembly. Accordingly, for use, the suture sleeve assembly may be assembled by threading lead body 12 through tubular sleeve 20 and collet member 22 to achieve a configuration as shown in FIG. 3. Thereafter, one may force collet member 22 to move axially into bore 36 of sleeve 20. Hook members 32 can be seen to exhibit angled surfaces on their sides facing away from the collet member 22, to facilitate their entry into bore 36, which is proportioned to force legs 30 into an inwardly biased position in which frictional gripping members 34 are pressed into the outer surface of lead body 12 for strong frictional retention thereof. Tubular sleeve 20 and collet member 22 are brought together until hook members 32 snap outwardly to engage an end of tubular sleeve 20, as shown in FIG. 2. In that configuration frictional gripping members 34 still provide adequate frictional retention to prevent longitudinal sliding of lead body 12 through sutute sleeve assembly 18. As hook members 32 snap into engagement with one end of tubular sleve 20, retention sleeve 28 preferably comes into engagement with sleeve 20 so that a tight-fitting, well-positioned, retained relationship is provided between tubular sleeve 20 and collet member 22, with legs 30 being forced inwardly to a degree sufficient to inpart strong frictional retention of lead body 12. While some degree of longitudinal movement or "play" between collet member 22 and sleeve may be permitted, it is preferred for this to be minimized so that they are essentially immovable one with the other.

After assembly of the suture sleeve of this invention with lead member 20 secured therein, the sutures 26 may be applied through the tissue 38 in which suture sleeve assembly 18 resides and around tubular sleeve 20 within groove 24 as previously described, for firm retention of lead body 12 and sleeve assembly 18 in their desired positions.

The above has been offered for illustrative purposes only and is not intended to limit the scope of the invention of this application, which is as defined in the claims below.

That which is claimed is:

1. A suture sleeve assembly for placement around an elongated lead body, to anchor said lead body in position relative to the adjacent tissue, which comprises:
a tubular sleeve having a bore;
a collet member, said collet member defining a plurality of axially extending legs residing in the bore of the tubular sleeve, said legs having inner surfaces, the inner surfaces of said legs defining frictional gripping members to engage a lead body positioned within said sleeve assembly; and means for retaining said collet member in a position with said legs occupying the bore of the tubular sleeve; said retaining means including outwardly extending hook members defined on the collet member adjacent the free ends of said legs, and a retention flange on the end of said collet member opposed to said free ends, said tubular sleeve being proportioned to that the legs pass through said sleeve to permit the hook members to engage one end thereof, while the retention flange engages the other end of said sleeve.

2. The suture sleeve assembly of claim 1 in which said tubular sleeve is made of elastomeric material, and said collet member is made of generally rigid material having sufficient flexibility whereby said legs can be forced by bending into frictionally engaging relation with a lead passing through said collet member.

3. The suture sleeve assembly of claim 1 in which the bore of said tubular sleeve is proportioned to bias said axially extending legs inwardly when the legs occupy the bore of said tubular sleeve, whereby an elongated lead body may be threaded through said collet member, and said axially extending legs may be forced inwardly by the bore of said tubular sleeve to engage said lead body by assembling the tubular sleeve and collet member after said tubular sleeve has been positioned at a predetermined position on said lead body.

4. A suture sleeve assembly for placement around an elongated lead body to anchor said lead body in position relative to the adjacent tissue, which comprises:
a tubular sleeve having a bore, said tubular sleeve having an outer surface and defining suture-receiving channel means on its outer surface to facilitate its retention in position by suture;
a collet member, said collet member defining a plurality of axially extending legs residing in the bore of the tubular sleeve, said legs having inner surfaces, the inner surfaces of said legs defining frictional gripping members to engage a lead body positioned within said sleeve assembly, said collet member defining outwardly extending hook members adjacent the free ends of said legs, and a retention flange on the end of said collet member opposed to said free ends, said tubular sleeve being proportioned whereby the legs pass through said sleeve to permit the hook members to engage one end thereof while the retention flange engages the other end of said sleeve, to retain the collet member precisely positioned with respect to said sleeve.

5. The suture sleeve assembly of claim 4 in which said tubular sleeve is made of elastomeric material, and said collet member is made of generally rigid material having sufficient flexibility whereby said legs can be forced by bending into frictionally engaging relation with a lead passing through said collet member.

6. The suture sleeve assembly of claim 4 in which the bore of said tubular sleeve is proportioned to bias said axially extending legs inwardly when the legs occupy the bore of said tubular sleeve, whereby an elongated lead body may be threaded through said collet member, and said axially extending legs may be forced inwardly by the bore of said tubular sleeve to engage said lead body by assembling the tubular sleeve and collet member after said tubular sleeve has been positioned at a predetermined position on said lead body.

* * * * *